United States Patent
Eguchi et al.

[19]

[11] Patent Number: 5,972,300

[45] Date of Patent: Oct. 26, 1999

[54] METHOD AND MEANS FOR RECOVERING HEAT IN THE PYROLYSIS OF 1,2-DICHLOROETHANE

[75] Inventors: Atsushi Eguchi; Fumio Akiya; Shohei Kojima, all of Ibaraki-ken, Japan

[73] Assignees: Kashima Vinyl Chloride Monomer Co., Ltd., Ibaraki-ken; Shin-Etsu Chemical Co., Ltd., Tokyo, both of Japan

[21] Appl. No.: 08/968,940

[22] Filed: Nov. 12, 1997

Related U.S. Application Data

[62] Division of application No. 08/815,123, Mar. 11, 1997, Pat. No. 5,728,906.

[30] Foreign Application Priority Data

Mar. 11, 1996 [JP] Japan ........................................ 8-82119

[51] Int. Cl.⁶ ............................... F28D 7/08; C07C 21/06
[52] U.S. Cl. ............................ 422/198; 422/203; 422/204
[58] Field of Search ..................................... 422/198, 200, 422/201–203, 229, 173, 204; 570/226

[56] References Cited

U.S. PATENT DOCUMENTS

| | | | |
|---|---|---|---|
| 3,896,182 | 7/1975 | Young | 570/226 |
| 4,014,947 | 3/1977 | Volodin et al. | 570/226 |
| 4,225,520 | 9/1980 | Riedl et al. | 570/226 |
| 4,590,318 | 5/1986 | Longhini | 570/226 |
| 4,665,243 | 5/1987 | Burks | 570/226 |
| 4,720,599 | 1/1988 | Hebgen et al. | 570/226 |
| 4,746,759 | 5/1988 | Dummer et al. | 570/226 |
| 5,188,739 | 2/1993 | Khan et al. | 210/781 |

FOREIGN PATENT DOCUMENTS

| | | |
|---|---|---|
| 1127669 | 7/1982 | Canada . |
| 0014920B1 | 12/1982 | European Pat. Off. . |
| 55-129233A | 6/1980 | Japan . |

*Primary Examiner*—Hien Tran
*Attorney, Agent, or Firm*—Birch, Stewart, Kolasch & Birch, LLP

[57] ABSTRACT

A process for the pyrolysis of 1,2-dichloroethane (EDC) in a pyrolysis furnace (1) involves feeding liquid EDC into a convection heat transfer tube (2) for preheating, channeling an intermediate flow of preheated EDC into a radiation heat transfer tube (3) for further heating, thereby pyrolyzing a part of EDC into vinyl chloride monomer, and discharging a decomposition gas flow from the pyrolysis furnace. Potential heat is recovered from the decomposition gas by using a double tube type heat exchanger (10) consisting of outer and inner tubes, that is, by channeling the intermediate flow through the outer tube (11), channeling the decomposition gas through the inner tube (15) for heat exchange between the intermediate flow and the decomposition gas, and feeding the heat acquired intermediate flow into the radiation heat transfer tube (3).

3 Claims, 2 Drawing Sheets

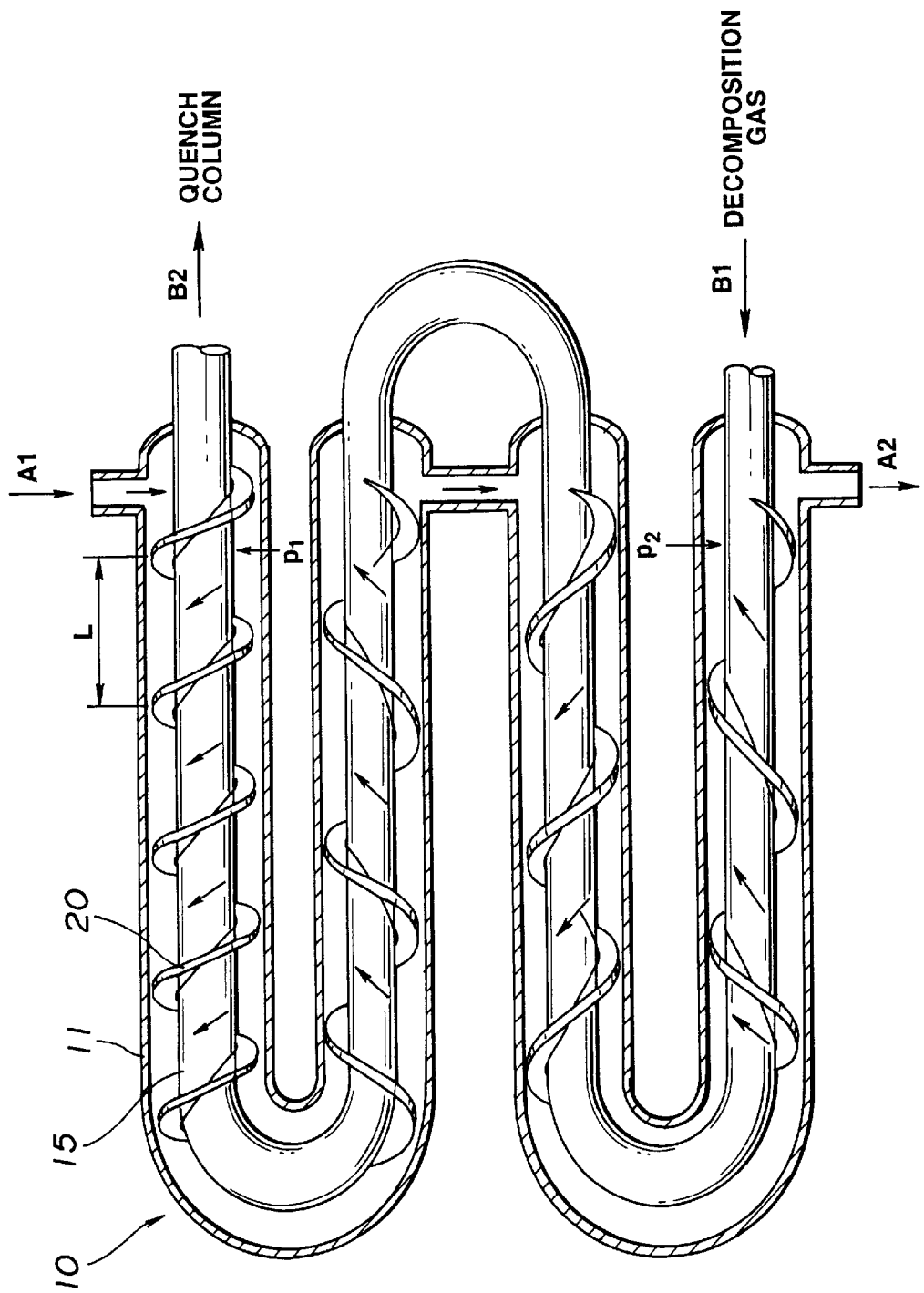

METHOD AND MEANS FOR RECOVERING HEAT IN THE PYROLYSIS OF 1,2-DICHLOROETHANE This application is a divisional of application Ser. No. 08/815,123, filed on Mar. 11, 1997, now U.S. Pat. No. 5,728,906, which issued on Mar. 17, 1998, the entire contents of which are hereby incorporated by reference.

BACKGROUND OF THE INVENTION

1. Field of the Invention

This invention generally relates to a process for the pyrolysis of 1,2-dichloroethane to form vinyl chloride monomer in a pyrolysis furnace. More particularly, it relates to a method and means for recovering heat from such a pyrolytic process by adding a heat exchanger to the furnace.

2. Prior Art

As is well known in the art, vinyl chloride monomer (to be abbreviated as VCM, hereinafter) is generally produced by pyrolyzing 1,2-dichoroethane (to be abbreviated as EDC, hereinafter) in a pyrolysis furnace. The pyrolysis furnace includes a convection heat transfer conduit extending in an upper convection heat transfer region, a radiation heat transfer conduit extending in a lower radiation heat transfer region, and means for heating the radiation heat transfer conduit. Liquid EDC is fed into the convection heat transfer conduit where EDC is preheated for vaporization, and then channeled into the radiation heat transfer conduit where the gaseous EDC is pyrolyzed to generate VCM and hydrogen chloride.

In this process, for the purpose of suppressing formation of by-product impurities and formation of carbon due to excessive decomposition, pyrolysis reaction is controlled to such an extent that about 50 to 60% of the EDC feed is decomposed. Then the decomposition gas exiting from the pyrolysis furnace mainly contains VCM, hydrogen chloride, and EDC. The gas available at the pyrolysis furnace outlet (to be referred to as decomposition gas, hereinafter) is generally at a temperature of about 450 to 550° C.

Various attempts were made in the prior art to recover the potential heat that the hot decomposition gas possesses for effective utilization of heat. For example, Japanese Patent Application Kokai (JP-A) No. 129233/1980 discloses a method for recovering potential heat from decomposition gas in an industrially acceptable manner. This method uses a heat exchanger for recovering heat from the decomposition gas and utilizes the recovered heat for heating EDC feed. When the high temperature the decomposition gas possesses is utilized for preheating and evaporating (or vaporizing) EDC, the fuel consumed in the pyrolysis furnace can be saved about 20 to 25%. This heat recovery method is quite advantageous from economic and environmental aspects.

The method of JP-A 129233/1980 for recovering potential heat in decomposition gas by means of a heat exchanger and utilizing the recovered heat for heating EDC feed is described in detail. After EDC is fed into a convection heat transfer region of the pyrolysis furnace for preheating EDC, the EDC is taken out of the furnace and fed to a heat exchanger which also receives the decomposition gas that has been heated hot, whereby heat is recovered from the decomposition gas. EDC is heated with the recovered heat for partial evaporation or vaporization. Thereafter, gaseous EDC is separated from the partially evaporated or vaporized EDC. The gaseous EDC is fed back to a radiation heat transfer region of the pyrolysis furnace. The heat exchanger used in this method is a single tube type heat exchanger having an inner tube extended in a jacket in a serpentine manner. Decomposition gas flows through the inner tube while liquid EDC is contained in the jacket. Since liquid EDC remains in the jacket of the single tube type heat exchanger, the amount of gaseous EDC taken out of the jacket is not always coincident with the amount of liquid EDC fed thereto. When the gaseous EDC is fed to the pyrolysis furnace, its flow rate must be controlled. Also the surface of liquid EDC in the jacket must be controlled. A new control loop is thus required. Undesirably, the control system becomes complex and the instrumentation cost is increased.

The method of JP-A 129233/1980 has another problem that since liquid EDC is evaporated or vaporized in the jacket of the heat exchanger, carbonaceous scale or carbon scale is likely to deposit on the inner wall of the jacket in contact with EDC. Undesirably the carbonaceous scale deposited on the inner wall reduces heat transfer. It is thus necessary to remove the carbonaceous deposit from the inner wall.

SUMMARY OF THE INVENTION

An object of the present invention is to provide a heat recovery method and system in a process for the pyrolysis of 1,2-dichloroethane, the method and system capable of effectively recovering and utilizing heat from the decomposition gas.

In connection with a heat recovery method of channeling an intermediate flow of liquid EDC, once heated in the convection heat transfer region of the pyrolysis furnace, to a heat exchanger and carrying out indirect heat exchange between the intermediate flow and the decomposition gas, the following requirements must be met in order to establish a novel technique capable of overcoming the drawbacks of the above-mentioned prior art. The requirements are (1) that the control system associated with the pyrolysis furnace is essentially simple and the control loop remains unchanged independent of whether or not a heat recovery means is provided, and (2) that the technique is effective for suppressing formation and deposition of carbonaceous scale in a heat exchanger.

In one aspect, the present invention pertains to a process for the pyrolysis of 1,2-dichloroethane in a pyrolysis furnace including a convection heat transfer region and a radiation heat transfer region by feeding liquid 1,2-dichloroethane into the convection heat transfer region where the liquid 1,2-dichloroethane is heated, channeling an intermediate flow of heated 1,2-dichloroethane into the radiation heat transfer region where the 1,2-dichloroethane is further heated, thereby pyrolyzing at least a part of 1,2-dichloroethane into vinyl chloride monomer, and discharging a decomposition gas containing the vinyl chloride monomer from the pyrolysis furnace. The invention provides a method for recovering potential heat from the decomposition gas comprising the steps of: Channeling the intermediate flow to a heat exchanger provided outside the pyrolysis furnace; introducing the decomposition gas into the heat exchanger whereby heat exchange takes place between the intermediate flow and the decomposition gas; and feeding the heat acquired intermediate flow into the radiation heat transfer region. The heat exchanger is a double tube type heat exchanger including an outer tube having an inlet and an outlet and an inner tube having an inlet and an outlet. The outer tube inlet is connected to an outlet of the convection heat transfer region through a single tube, and the outer tube outlet is connected to an inlet of the radiation heat transfer region -through a single tube, thereby forming a single flowpath extending from the outlet of the convection heat transfer region to the inlet of the radiation heat transfer region through the outer tube. The intermediate flow is passed through the single flowpath, and the decomposition gas is passed through the inner tube of the double tube type heat exchanger.

In another aspect, the present invention pertains to a system for the pyrolysis of 1,2-dichloroethane comprising a pyrolysis furnace including an upper convection heat transfer region, a lower radiation heat transfer region, a convection heat transfer conduit in the convection heat transfer region having an inlet for receiving and passing liquid 1,2-dichloroethane for heating and an outlet for discharging an intermediate flow of heated 1,2-dichloroethane, a radiation heat transfer conduit in the radiation heat transfer region having an inlet for receiving and passing the intermediate flow for further heating to pyrolye at least a part of 1,2-dichloroethane into vinyl chloride monomer and an outlet for discharging a decomposition gas flow containing the vinyl chloride monomer therefrom, and means for heating the radiation heat transfer conduit, and a heat exchanger disposed outside the pyrolysis furnace for receiving the intermediate flow and the decomposition gas whereby heat exchange takes place between the intermediate flow and the decomposition gas, and for feeding the heat acquired intermediate flow into the radiation heat transfer region. The invention provides a means for recovering potential heat from the decomposition gas wherein the heat exchanger is a double tube type heat exchanger which is disposed at an intermediate height between the position of the outlet of the convection heat transfer conduit and the position of the inlet of the radiation heat transfer conduit and includes an outer tube having an inlet and an outlet and an inner tube having an inlet and an outlet. The outer tube inlet is connected to the outlet of the convection heat transfer conduit through a single tube, and the outer tube outlet is connected to the inlet of the radiation heat transfer conduit through a single tube, thereby forming a horizontal and downward single flowpath extending from the outlet of the convection heat transfer conduit to the inlet of the radiation heat transfer conduit through the outer tube. The intermediate flow is passed through the single flowpath, and the decomposition gas is passed through the inner tube of the double tube type heat exchanger.

In a method and system for recovering potential heat from a decomposition gas flow in a process for the pyrolysis of EDC by channeling an intermediate flow of EDC from the pyrolysis furnace to a heat exchanger outside the pyrolysis furnace, introducing a decomposition gas flow from an outlet of the pyrolysis furnace into the heat exchanger whereby heat exchange takes place between the intermediate flow and the decomposition gas flow, and feeding the intermediate flow back to the pyrolysis furnace, the present invention uses a double tube type heat exchanger in which a single tube provides a flowpath for EDC. Then the amount of partially or entirely evaporated or vaporized EDC taken out of the heat exchanger is coincident with the amount of liquid EDC fed into the heat exchanger. Then simply feeding the EDC which has been partially or entirely evaporated or vaporized through the heat exchanger to the radiation heat transfer tube of the pyrolysis furnace is acceptable. There is no need to control the flow rate of gaseous EDC fed back to the pyrolysis furnace.

A key is to eliminate any region where the liquid EDC stays. The stay of liquid ensures complete separation between gas and liquid, but requires to control the liquid surface and the flow rate of gas, eventually requiring a new control loop. To avoid such inconvenience, the invention uses a heat exchanger of the double tube type in which decomposition gas is passed through the inner tube and EDC is passed through the outer tube. This is partially because decomposition gas should be passed through the inner tube of the double tube type heat exchanger in order to prevent the decomposition gas from forming and depositing a carbonaceous scale on the tube wall.

The reason why the invention uses a heat exchanger of the double tube type is described below. Briefly stated, such a heat exchanger is employed to meet the necessity to maintain the gaseous EDC flow fed back to the pyrolysis furnace at a constant mass flow rate. Since the heat transfer tube in the radiation heat transfer region is directly exposed to flame in the pyrolysis furnace, that heat transfer tube encounters a danger of overheating failure even when the flow rate of internal fluid is reduced for only a very short time. Then the flow rate of gaseous EDC fed into the radiation heat transfer tube must be strictly controlled. In the practice of the invention, the flow rate of EDC is controlled in a liquid state prior to supply to the convection heat transfer region of the pyrolysis furnace, but not in a vapor state after evaporation in the heat exchanger. Then the heated EDC must flow at a constant mass flow rate both before and after evaporation under the impetus of continuously extruding (or forcing) flow. Since the decomposition gas flows inside the inner tube, the concept of maintaining a constant mass flow rate outside the inner tube is accomplished by employing a double tube type heat exchanger capable of providing a flowpath of any desired cross-sectional area and preventing static residence of liquid.

The flowpath for EDC is a single flowpath when it is considered as a series of flow units extending from the pyrolysis furnace to the heat exchanger and back to the pyrolysis furnace. The single flowpath also ensures to maintain the fluid flow back to the pyrolysis furnace at a constant mass flow rate.

Another distinction of the present invention from the prior art method is that EDC can be equally handled independent of whether it is completely or not completely evaporated in the heat exchanger. More particularly, liquid EDC fed into the heat exchanger is partially or entirely evaporated. Since a constant mass flow rate is maintained, a rate of evaporation does little affect the pyrolysis furnace. In this context, the present invention can be regarded as a system wherein the heat transfer tube in the evaporation zone of the pyrolysis furnace is replaced by an external heat exchanger.

This leads to important advantages that system design is given a degree of freedom and long-term continuous operation is possible. Usually, a prior art heat exchanger gradually loses its heat transfer capacity as carbonaceous scale deposits on the decomposition gas side. In the event where EDC is completely evaporated, the amount of EDC vapor which can be fed back to the pyrolysis furnace decreases with the progress of contamination. This leads to the drawback that load downing is unavoidable or a complex control system of providing a trim burner in the convection heat transfer region (adjacent to the inlet of the heat exchanger) for preheating must be employed. In contrast, the system of the present invention need not change the control method independent of whether EDC is completely or not completely evaporated in the heat exchanger since the EDC flowpath of the heat exchanger can be considered as a flowpath continuous and equivalent to the heat transfer tube in the pyrolysis furnace. The system of the present invention is equally applicable even when the EDC entering the heat exchanger has been partially evaporated in the convection heat transfer region of the pyrolysis furnace.

The apparatus of the invention presents a characteristic advantage of safety since the double tube type heat exchanger is disposed at an intermediate height between the position of the outlet of the convection heat transfer conduit and the position of the inlet of the radiation heat transfer conduit, the inlet of the heat exchanger outer tube is connected to the outlet of the convection heat transfer conduit through a single tube, the outlet of the heat exchanger outer tube is connected to the inlet of the radiation heat transfer conduit through a single tube, thereby forming a horizontally and downwardly oriented single flowpath extending from the outlet of the convection heat transfer conduit to the inlet of the radiation heat transfer conduit through the outer tube. Since the method of the invention is mainly intended for evaporation of EDC by heat recovery, the EDC flowpath contains liquid EDC therein. The EDC flowpath which is horizontally and downwardly oriented avoids stagnation of the fluid. Even when EDC supply is stopped, the liquid then in the convection heat transfer region will spontaneously flow to the radiation heat transfer region under gravity. The system remains safe.

For example, not a few troubles of liquid EDC supply being suddenly stopped as by a failure of a flow rate control valve associated with liquid EDC occur during normal operation of the pyrolysis furnace. In such an event, a common practice is to instantaneously interrupt fuel supply and shut down the furnace. In the worst case wherein the control circuit therefor does not perform normally, the heat transfer tube can be blown up by overheating. The furnace of the structure constructed according to the invention can avoid such danger as compared with conventional structures. In the present invention, the convection heat transfer region of the pyrolysis furnace to which liquid EDC is fed is a liquid preheating region and the heat transfer tube is full of the liquid. When EDC supply to the furnace is stopped, the liquid held in the convection heat transfer region spontaneously flows down to the hotter radiation heat transfer region under gravity so that the heat transfer tube of the radiation heat transfer region subsequently receives EDC supply though temporarily. The gravity drained EDC has a sufficient latent heat to restrain the heat transfer tube from being overheated, ensuring a safety feature.

BRIEF DESCRIPTION OF THE DRAWINGS

FIG. 2 is a partially cross-sectional front elevation of a heat exchanger.

DESCRIPTION OF THE PREFERRED EMBODIMENT

Figure 1:
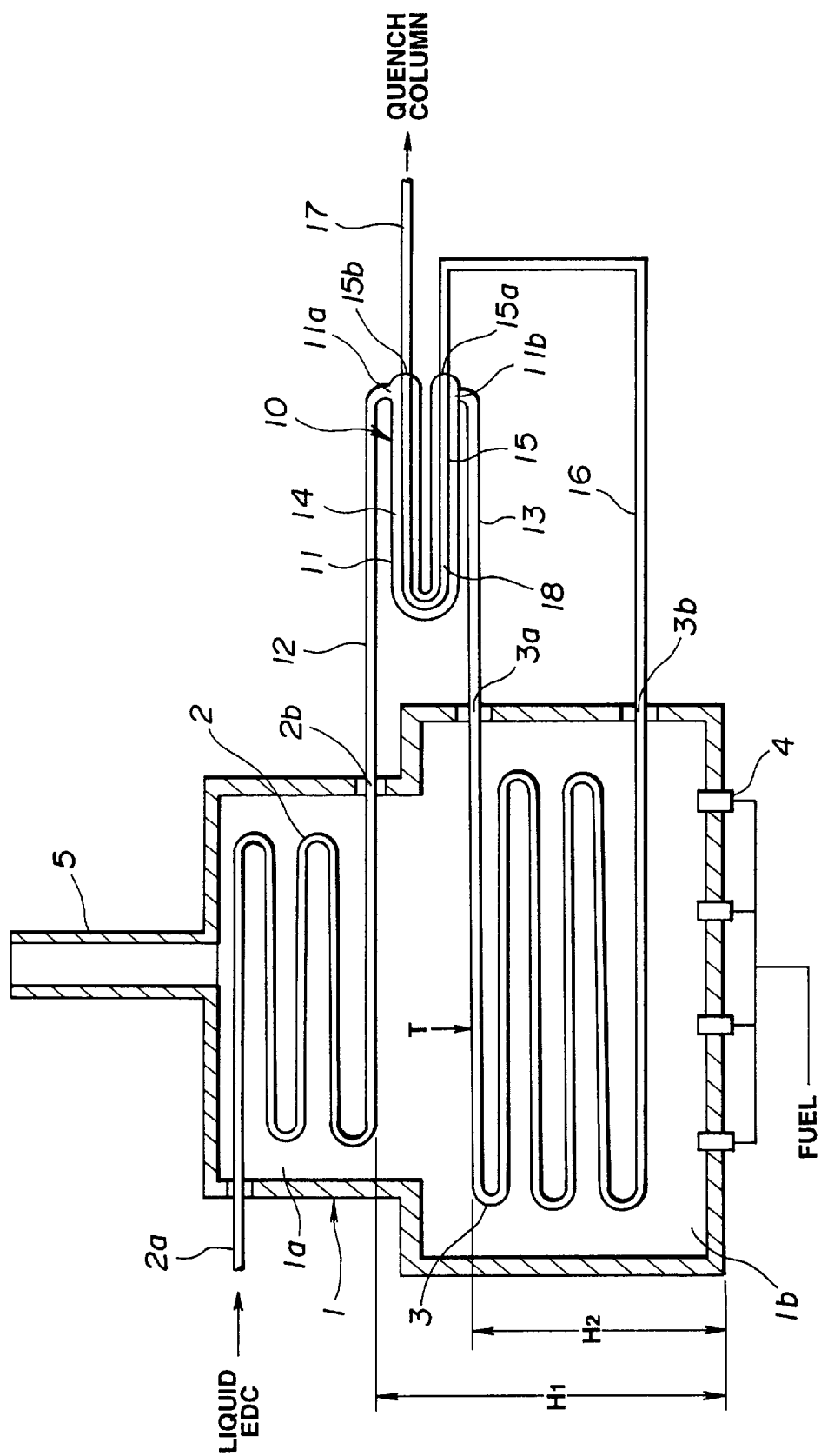
FIG. 1 is a schematic cross-sectional view of a furnace according to one embodiment of the invention.

Referring to FIG. 1, there is illustrated a system according to one embodiment of the invention. The system includes a furnace 1 for the pyrolysis of EDC. The pyrolysis furnace 1 includes an upper portion defining a convection heat transfer region 1a and a lower portion defining a radiant heat transfer region 1b. A serpentine convection heat transfer tube 2 having an inlet or upper end 2a and an outlet or lower end 2b is disposed in the convection heat transfer region 1a. A serpentine radiant heat transfer tube 3 having an inlet or upper end 3a and an outlet or lower end 3b is disposed in the radiant heat transfer region 1b. Heater means in the form of burners 4 is disposed at the bottom of the pyrolysis furnace 1 for heating the radiant heat transfer tube 3. The pyrolysis furnace 1 further includes a chimney 5 at the top of the upper portion.

Disposed outside the furnace 1 is a double tube type heat exchanger 10. The heat exchanger 10 is located at an intermediate height position between a height H1 corresponding to the outlet or lower end 2b of the convection heat transfer tube 2 and a height H2 corresponding to the inlet or upper end 3a of the radiant heat transfer tube 3. The heat exchanger 10 includes a U-shaped outer tube 11 having an inlet end 11a and an outlet end 11b and a U-shaped inner tube 15 extending through the outer tube 11 and having an inlet end 15a and an outlet end 15b. The inlet end 11a of the outer tube 11 is connected to a first single tube 12 which is integrally connected to the outlet end 2b of the convection heat transfer tube 2. The outlet end 11b of the outer tube 11 is connected to a second single tube 13 which is integrally connected to the inlet end 3a of the radiant heat transfer tube 3. The first single tube 12, outer tube 11 and second single tube 13 form a single flowpath 14 which constitutes an intermediate flow channel for the EDC preheated in the convection heat transfer tube 2. This single flowpath 14 extends horizontally, downwardly and then horizontally in a forward direction, but not upwardly so that liquid will spontaneously flow under gravity from the outlet end 2b of the convection heat transfer tube 2 to the inlet end 3a of the radiant heat transfer tube 3. The inlet end 15a of the inner tube 15 is connected to a single tube 16 which is integrally connected to the outlet end 3b of the radiant heat transfer tube 3. The outlet end 15b of the inner tube 15 is connected to a quenching column (not shown) through a single tube 17. The inner tube 15 constitutes a decomposed gas flowpath 18.

When EDC is pyrolyzed using the above-mentioned system, liquid EDC is first introduced into the convection heat transfer tube 2 in the pyrolysis furnace 1 from its inlet end 2a whereupon liquid EDC is preheated with convection heat in the furnace 1. Specifically, liquid EDC is introduced into the convection heat transfer tube 2 under a pressure of 25 to 40 kg/cm$^2$G and preheated to a temperature of about 150 to 300° C.

The preheated EDC then flows through the single flowpath (intermediate flow channel) 14 as a liquid or partially evaporated (gasified) intermediate flow whereby it is introduced into the outer tube 11 of the heat exchanger 10 outside the furnace 1. Since decomposition gas at a high temperature (of usually 450 to 550° C.) having undergone pyrolysis reaction to be described later flows through the inner tube 15 of the heat exchanger 10, the intermediate flow exchanges heat with the hot decomposition gas whereby it is heated to about 200 to 350° C. Then the intermediate flow in a partially or entirely evaporated state exits from the outer tube 11 and enters the radiant heat transfer tube 3 in the pyrolysis furnace 1. Since the radiant heat transfer tube 3 is heated by flames of the burners 4 at the bottom of the pyrolysis furnace 1, the EDC entering the radiant heat transfer tube 3 is herein completely evaporated (gasified) and further, a portion thereof undergoes pyrolysis reaction whereby it is decomposed into vinyl chloride and hydrogen chloride. The decomposition gas having undergone pyrolysis reaction is at a high temperature of 450 to 550° C. The decomposition gas exits from the pyrolysis furnace 1, passes through the inner tube 15 of the double tube type heat exchanger 10 where the gas is cooled, and further proceeds to the quenching column where the gas is further cooled.

In the system according to the invention, the outer tube of the double tube type heat exchanger is used as a flow channel for EDC and the inner tube is used as a flow channel for decomposition gas. The EDC having passed through the convection heat transfer tube is introduced into the double tube type heat exchanger where it is heated into a partially or entirely evaporated (gasified) state. Preferably EDC passes through the double tube type heat exchanger at a fluid linear velocity of 0.5 to 20 m/s, especially 0.9 to 12 m/s. A fluid linear velocity outside this range would cause some troubles such as a reduced heat transfer capacity and an increased pressure loss.

FIG. 2 shows one exemplary structure of a heat exchanger which can establish such conditions at low cost. The heat exchanger 10 includes an outer tube 11 in the form of two U-shaped tubes 11 connected in series and an inner tube 15 extending through the outer tube 11. A helical guide or screw 20 is disposed around the inner tube 15 to define a helical path between the outer and inner tubes 11 and 15. Decomposition gas enters the inner tube 15 as a flow B1, passes therethrough, and exits from the inner tube as a flow B2. EDC enters the outer tube 11 as a flow A1, passes therethrough, and exits from the outer tube as a flow A2. The helical guide 20 is provided for the purpose of establishing a desired linear velocity for the fluid. The EDC flows in a helical manner as shown by arrows in FIG. 2. The linear velocity of the fluid increases as the pitch L of the helical guide 20 is reduced. The fluid flow is slowed down as the helical pitch L is increased.

The linear velocity of the fluid flowing through the outer tube is higher at a downstream position than at an upstream position due to the progress of evaporation. It is then preferred that the pitch L of the helical guide 20 be increased in a downstream direction as shown in FIG. 2. More specifically, the ratio of the helical pitch L at the EDC outlet to the helical pitch L at the EDC inlet preferably ranges from 1.2/1 to 4/1, more preferably from 1.3/1 to 2.5/1.

It is not necessary that the helical guide 20 be in close fit to the outer and inner tubes 11 and 15. When the differential thermal expansion between the outer and inner tubes 11 and 15 is taken into account, it is preferred for safety to leave a gap between the helical guide 20 and the outer and inner tubes 11 and 15. A gap of 1 to 5 mm has no substantial influence on the function of the helical guide. It is noted that steady rest means for preventing the inner tube from vibration is separately provided if a substantial gap is left.

The bent tube structure shown in FIG. 2 can accommodate the difference in longitudinal expansion between the outer and inner tubes 11 and 15. However, the structure of the outer tube 11 is not limited to that of FIG. 2. For example, straight sections of the double tube structure may be connected through expansion joints.

It is noted that liquid EDC fed to the convection heat transfer tube 2 of the pyrolysis furnace 1 desirably has an iron concentration of 0.5 ppm or less, more desirably 0.1 ppm or less. By limiting the iron concentration of liquid EDC to 0.5 ppm or less, deposition of carbon scale on the inner wall of the outer tube 11 of the double tube type heat exchanger 10 is minimized. Therefore, if the liquid EDC fed to the convection heat transfer tube 2 of the pyrolysis furnace 1 is previously managed to an iron concentration of 0.5 ppm or less, the outer tube of the double tube type heat exchanger 10 may be of a simple structure rather than a complex structure configured for ease of cleaning.

EXAMPLE

An example of the present invention is given below by way of illustration and not by way of limitation.

Pyrolysis of EDC was carried out in the system shown in FIG. 1 in which the double tube type heat exchanger shown in FIG. 2 was incorporated. In the double tube type heat exchanger shown in FIG. 2, the inner tube had an outer diameter of 19.1 cm and the outer tube had an inner diameter of 33.4 cm. The helical guides disposed within the outer tube had a pitch L which was 15 cm in an upstream section of 5 m long from the EDC inlet A1 (33 turns), 20 cm in an intermediate section of 15 m long (75 turns), and 25 cm in a downstream section of 20 m long extending from the intermediate section to the EDC outlet A2 (80 turns). The helical guides were fixedly secured to the inner tube and separated a gap of 3 mm from the outer tube.

Liquid EDC at a temperature of 125° C. was fed into the convection heat transfer tube 2 under a pressure of 33.2 kg/cm$^2$G at a flow rate of 46 ton/hr. The liquid EDC feed had an iron concentration of 0.05 ppm. The EDC was preheated to 245° C. in the convection heat transfer tube 2 before it was introduced into the outer tube 11 of the double tube type heat exchanger 10.

On the other hand, decomposition gas "B1" at a temperature of 475° C. was introduced into the inner tube 15 of the heat exchanger 10 at a flow rate of 46 ton/hr and a linear velocity of 27.2 m/s. Heat exchange took place between the EDC in the outer tube 11 and the decomposition gas in the inner tube 15. As a result, the decomposition gas was cooled to 370° C. while it was passing through the inner tube 15 of the heat exchanger 10. The thus cooled decomposition gas "B2" was then delivered to a quenching column where it was further cooled. On the other hand, the EDC fed into the outer tube 11 of the heat exchanger 10 at 245° C. was converted into vapor partially containing liquid while it was passing through the outer tube 11 of the heat exchanger 10, and then introduced into the radiation heat transfer tube 3 at 250° C. The EDC fed into the operating outer tube was vaporized at a percent vaporization of about 90% by weight. The EDC flow through the operating outer tube had a linear velocity of 1.2 m/s at the first turn of the helical guide depicted as p1 in FIG. 2 and a linear velocity of 9.0 m/s at the last turn of the helical guide depicted as p2 in FIG. 2. The system was continuously operated for 6 months. During the continuous operation, the temperature of the radiation heat transfer tube 3 at a point T (FIG. 1) was maintained stable in the range of 350° C.±5° C. The operation experienced no disturbances as by stagnation of liquid EDC feed.

At the end of operation, the double tube type heat exchanger 10 was disassembled to inspect the outer tube, finding no carbon scale on the inner wall of the outer tube.

The double tube type heat exchanger 10 had an overall coefficient of heat transfer which was 1.5 to 2.5 times greater than simple immersion in an EDC pool. The pressure loss was about 0.05 kg/cm$^2$ per meter of the uncovered tube and gave rise to no substantial problem in most cases.

The present invention has several advantages that (1) operation is easy because a heat recovery means provided herein does not require an extra control system, (2) deposition of carbonaceous scale on the EDC side is essentially eliminated, and (3) the structural advantage of safety inherent to the pyrolysis furnace is maintained.

Japanese Patent Application No. 82119/1996 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. An apparatus for recovering potential heat from a decomposition gas in a system for the pyrolysis of 1,2-dichloroethane comprising a pyrolysis furnace including an upper convention heat transfer region, a lower radiation heat transfer region, a convection heat transfer conduit in the convection heat transfer region having an inlet for receiving and passing liquid 1,2-dichloroethane for heating and an outlet for discharging an intermediate flow of heated 1,2-dichloroethane, a radiation heat transfer conduit in the radiation heat transfer region having an inlet for receiving and passing the intermediate flow for further heating to pyrolyze at least a part of 1,2-dichloroethane into vinyl chloride monomer and an outlet for discharging a decomposition gas flow containing the vinyl chloride monomer therefrom, and means for heating the radiation heat transfer conduit, and a heat exchanger disposed outside the pyrolysis furnace for receiving the intermediate flow and the decomposition gas whereby heat exchange takes place between the intermediate flow and the decomposition gas, and for feeding the heat acquired intermediate flow into the radiation heat transfer region, wherein the heat exchanger is a double tube heat exchanger which is disposed at an intermediate height between the position of the outlet of said convection heat transfer conduit and the position of the inlet of said radiation heat transfer conduit and includes an outer tube having an inlet and an outlet and an inner tube having an inlet and an outlet, said double tube heat exchanger including a helical guide disposed between the outer and inner tubes and having a smaller pitch near the outer tube inlet and a greater pitch near the outer tube outlet, the outer tube inlet is connected to the outlet of the convection heat transfer conduit through a single tube, the outer tube outlet is connected to the inlet of the radiation heat transfer conduct through a single tube, thereby forming a horizontal and downward single flowpath extending from the outlet of the convection heat transfer conduit to the inlet of the radiation heat transfer conduit through the outer tube, the intermediate flow is passed through the single flowpath, and the decomposition gas is passed through the inner tube of said double tube heat exchanger.

2. The apparatus of claim 1, wherein the ratio of the helical pitch L at the outer tube outlet to the helical pitch L at the outer tube inlet ranges from 1.2/1 to 4/1.

3. The apparatus of claim 2, wherein the ratio of the helical pitch L at the outer tube outlet to the helical pitch L at the outer tube inlet ranges from 1.3/1 to 2.5/1.

* * * * *